(12) United States Patent
Yang

(10) Patent No.: US 10,791,970 B2
(45) Date of Patent: Oct. 6, 2020

(54) DEVICE, METHOD, AND SYSTEM TO MEASURE BLOOD GLUCOSE

(71) Applicant: PHILOSYS CO., LTD., Jeollabuk-do (KR)

(72) Inventor: Jung Yun Yang, Gyeonggi-do (KR)

(73) Assignee: PHILOSYS CO., LTD., Jeollabuk-Do (KR)

(*) Notice: Subject to any disclaimer, the term of this patent is extended or adjusted under 35 U.S.C. 154(b) by 119 days.

(21) Appl. No.: 16/100,599

(22) Filed: Aug. 10, 2018

(65) Prior Publication Data
US 2019/0282138 A1   Sep. 19, 2019

(30) Foreign Application Priority Data
Mar. 14, 2018   (KR) .................. 10-2018-0029852

(51) Int. Cl.
| | |
|---|---|
| *A61B 5/145* | (2006.01) |
| *G01N 33/66* | (2006.01) |
| *H04L 27/10* | (2006.01) |
| *A61B 5/15* | (2006.01) |
| *A61B 5/00* | (2006.01) |
| *H04M 1/725* | (2006.01) |

(52) U.S. Cl.
CPC ......... *A61B 5/14532* (2013.01); *G01N 33/66* (2013.01); *H04L 27/10* (2013.01); *A61B 5/150358* (2013.01); *A61B 5/6826* (2013.01); *A61B 5/6898* (2013.01); *A61B 2560/0443* (2013.01); *H04M 1/72527* (2013.01); *H04R 2420/09* (2013.01)

(58) Field of Classification Search
None
See application file for complete search history.

(56) References Cited

U.S. PATENT DOCUMENTS

| | | | | |
|---|---|---|---|---|
| 2003/0086074 | A1* | 5/2003 | Braig ................. | A61B 10/0045 356/39 |
| 2009/0099787 | A1* | 4/2009 | Carpenter .......... | A61B 5/14532 702/19 |
| 2013/0012796 | A1* | 1/2013 | Kak .................... | A61B 5/6898 600/365 |
| 2013/0217983 | A1* | 8/2013 | Rebec ................. | A61B 5/14532 600/316 |
| 2013/0274581 | A1* | 10/2013 | Choi .................. | A61B 5/14532 600/365 |
| 2016/0088136 | A1* | 3/2016 | Di Donato .............. | H04M 1/21 600/365 |

(Continued)

FOREIGN PATENT DOCUMENTS

KR          101658800 B1      9/2016

OTHER PUBLICATIONS

English translation of KR-101658800-B1. (Year: 2016).*
(Continued)

*Primary Examiner* — Etsub D Berhanu
*Assistant Examiner* — Aurelie H Tu (57) ABSTRACT

Disclosed is a blood glucose measuring device, method, and system. In response to a connection of a blood glucose measuring module to a socket of the blood glucose measuring device being detected, the blood glucose measuring device may receive a data signal from the blood glucose measuring module and read a bit of the data signal based on a period of data signal.

12 Claims, 6 Drawing Sheets

(56) References Cited

U.S. PATENT DOCUMENTS

2017/0000349 A1\* 1/2017 Krief .................... A61B 5/6898
2017/0164878 A1\* 6/2017 Connor ................. G09B 23/28

OTHER PUBLICATIONS

Nemiroski et al., "Universal mobile electrochemical detector designed for use in resource-limited applications" CrossMark Jun. 30, 2014—16 pages.

Sun et al., "An efficient power harvesting mobile phone-based electrochemical biosensor for point-of-care health monitoring" Elsevier 2016—10 pages.

\* cited by examiner

DEVICE, METHOD, AND SYSTEM TO MEASURE BLOOD GLUCOSE

CROSS-REFERENCE TO RELATED APPLICATION(S)

This application claims the priority benefit of Korean Patent Application No. 10-2018-0029852 filed on Mar. 14, 2018, in the Korean Intellectual Property Office, the disclosure of which is incorporated herein by reference for all purposes.

BACKGROUND

1. Field

One or more example embodiments relate to blood glucose measuring technology using a blood glucose measuring module.

2. Description of Related Art

Recently, there is a growing number of people suffering from adult diseases such as diabetes, hyperlipidemia, thrombosis, and the like due to westernized dietary habits, and is also a growing number of young women suffering from iron-deficiency anemia due to excessive dieting. A simple way of determining the severity of such diseases is to measure biological substances or components in blood. For example, such a biological component measurement may be used to determine amounts of various components in blood in some cases of a high blood glucose level, anemia, blood coagulation, and the like, and determine whether an amount of a certain component is in its normal range or abnormal range. Thus, an ordinary person, or a general user, may determine whether there is abnormality in blood without having to go to a hospital.

One of simplest methods of the biological component measurement is to collect blood from a fingertip and inject the collected blood into a strip to be inserted into a biosensor, and then perform a quantitative analysis of an output signal using an electrochemical method or a photometric method. This simplest method may be suitable for a general user who does not have expertise in this sort of technical field because a result of the analysis, for example, measured amounts of components, is displayed on a measurer.

For the biological component measurement, a biosensor may be used in conjunction with a smart device. Thus, there is a desire for technology for solving poor communication that may occur due to a difference in amplitude of data received by a socket of the smart device from the biosensor.

SUMMARY

An aspect of the present disclosure provides a blood glucose measuring device configured to receive, from a blood glucose measuring module configured to measure blood glucose, a data signal indicating a blood glucose level, when connected to the blood glucose measuring module.

The blood glucose measuring device may read a bit of the data signal based on a period of the data signal received from the blood glucose measuring module.

The blood glucose measuring device may read the bit of the data signal based on a sampling point in a target interval of the data signal.

The blood glucose measuring device may exclude, from an analysis, a sampling point which is not in the target interval of the data signal.

The blood glucose measuring device may determine the target interval based on a slope of the data signal.

Herein, a threshold range for the number of sampling points detected in a target interval may be set based on a type of blood glucose measuring device.

According to an aspect, there is provided a blood glucose measuring device including a socket to be connected to a plug of a blood glucose measuring module configured to measure a blood glucose level, and a processor configured to receive a data signal from the blood glucose measuring module and read a bit of the data signal based on a period of the data signal, when a connection of the blood glucose measuring module to the socket is detected.

After the connection of the blood glucose measuring module to the socket is established and a start signal is received, the processor may receive a series of data signals in sequential order until an end signal is received.

The processor may determine the bit of the data signal to be 0 in response to the data signal having a first period, and determine the bit of the data signal to be 1 in response to the data signal having a second period different from the first period.

The processor may determine the period of the data signal based on a change in slope of the data signal.

The processor may determine, to be a slope corresponding to a current timeslot of the data signal, a differential value between a signal magnitude value corresponding to the current timeslot of the data signal and a signal magnitude value corresponding to a previous timeslot of the data signal.

The processor may determine a target interval based on a change in slope of the data signal, and determine the period of the data signal based on the number of sampling points detected in the target interval.

The processor may determine the target interval based on a first inflection point at which a slope sign of the data signal is initially inverted and a second inflection point at which a slope sign of the data signal is secondly inverted.

The processor may determine the data signal to have the first period in response to the number of sampling points detected during the target interval being in a first threshold range, and may determine the data signal to have the second period in response to the number of sampling points detected during the target interval being in a second threshold range.

The processor may determine the first threshold range and the second threshold range based on a device parameter of the blood glucose measuring device.

In response to the connection of the blood glucose measuring module to the blood glucose measuring device, the processor may receive a pilot signal from the blood glucose measuring module during a calibration time, and determine the first threshold range and the second threshold range based on the number of sampling points detected during a target interval of the pilot signal.

In response to an inflection point not being detected from the data signal, the processor may be configured not to perform an analysis of sequence data including the data signal.

The processor may exclude, from the reading, a sampling point that is not in the target interval of the data signal.

According to another aspect, there is provided a blood glucose measuring method including receiving a data signal from a blood glucose measuring module in response to a connection of the blood glucose measuring module to a socket of a blood glucose measuring device being detected, and reading a bit of the data signal based on a period of the data signal.

According to still another aspect, there is provided a blood glucose measuring system including a blood glucose measuring module configured to measure a blood glucose level in blood absorbed in a test strip and transmit a data signal indicating the measured blood glucose level to a blood glucose measuring device in response to a connection to the blood glucose measuring device, and the blood glucose measuring device configured to receive the data signal and read a bit of the data signal based on a period of the data signal in response to the connection to the blood glucose measuring module.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only and is not to be used to limit the disclosure. As used herein, the articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Although terms such as "first," "second," "third," A, B, (a), (b), and the like may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing. As used herein, the term "and/or" includes any one and any combination of any two or more of the associated listed items.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Figure 1:
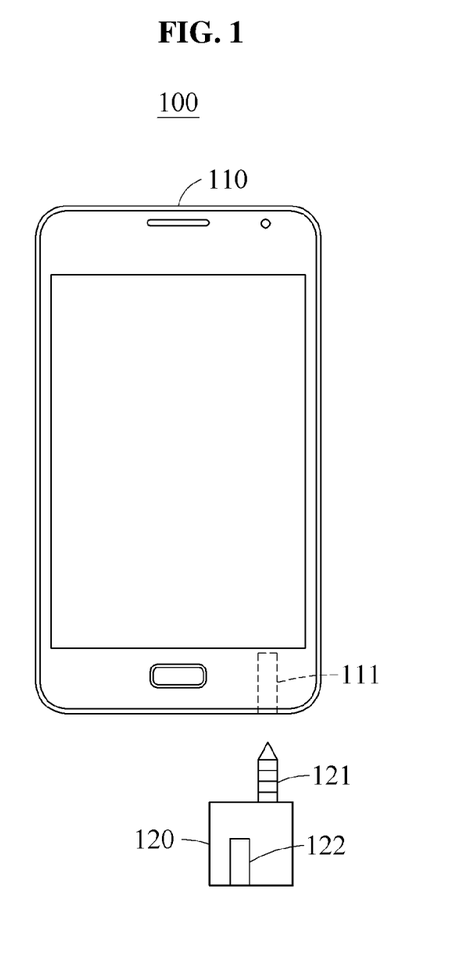
FIG. 1 is a diagram illustrating an example of a blood glucose measuring system according to an example embodiment.

FIG. 1 is a diagram illustrating an example of a blood glucose measuring system according to an example embodiment.

Referring to FIG. 1, a blood glucose measuring system 100 includes a blood glucose measuring device 110 and a blood glucose measuring module 120.

The blood glucose measuring device 110 may be a device to be combined with or connected to the blood glucose measuring module 120, and includes a socket 111 to be connected to a plug 121 of the blood glucose measuring module 120. For example, the blood glucose measuring device 110 may be embodied by a smart device, such as, for example, a smartphone, and includes a display configured to display a result of measuring a blood glucose level and a power supply configured to supply power. The socket 111 of the blood glucose measuring device 110 may be, for example, a microphone socket.

The blood glucose measuring device 110 may receive, from the blood glucose measuring module 120, sequence data indicating a blood glucose level measured by the blood glucose measuring module 120. The sequence data may also be referred to as blood glucose data. The blood glucose measuring device 110 may receive a series of data signals in sequential order. The blood glucose measuring device 110 may read the data signals, and determine a bit indicated by each of the data signals. Herein, a bit indicated by each data signal, or a bit of each data signal, may indicate a value 0 or 1, for example.

The blood glucose measuring device 110 may store a blood glucose measurement application program that may process and manage the sequence data indicating the blood glucose level.

Through the connection of the plug 121 of the blood glucose measuring module 120 to the socket 111 of the blood glucose measuring device 110, the blood glucose measuring module 120 may use an input, an output, and power of the blood glucose measuring device 110. Herein, data communication between the blood glucose measuring device 110 and the blood glucose measuring module 120 may be performed through a frequency-shift keying (FSK) scheme, but not limited thereto. A method for the data communication may be designed variously based on a purpose and means of use.

For example, the socket 111 may be embodied as a phone jack socket or a port to be connected to a phone jack plug or a pin plug, respectively, that is provided as the plug 121 of the blood glucose measuring module 120. However, types and forms of the socket 111 of the blood glucose measuring device 110 are not limited to the examples described in the foregoing. A pin-based connection structure may be embodied as a structure in which the blood glucose measuring device 110 includes the plug 121 and the blood glucose measuring module 120 includes the socket 111.

The blood glucose measuring module 120 may measure a blood glucose level in blood absorbed in a test strip, and transmit a data signal indicating the measured blood glucose level to the blood glucose measuring device 110 when being connected to the blood glucose measuring device 110. The blood glucose measuring module 120 may be used by being connected to the socket 111 of the blood glucose measuring device 110. For example, when the plug 121 of the blood glucose measuring module 120 is connected to the socket 111 of the blood glucose measuring device 110, the connection of the blood glucose measuring module 120 to the blood glucose measuring device 110 may be established. In response to the connection of the blood glucose measuring module 120 to the blood glucose measuring device 110 being detected, the blood glucose measuring module 120 may measure and calculate the blood glucose level in blood absorbed in the test strip using power supplied from the power supply of the blood glucose measuring device 110. The blood glucose measuring module 120 may then transmit, to the blood glucose measuring device 110, the sequence data including information indicating the measured blood glucose level.

The blood glucose measuring module 120 includes a main body, a strip inserter 122, and the plug 121.

The main body of the blood glucose measuring module 120 includes a blood glucose measurer configured to measure a blood glucose level in blood absorbed in the test strip, and a central processor configured to calculate and transmit a result of measuring the blood glucose level. The main body of the blood glucose measuring module 120 may be reduced in size and lightened in weight because it does not need a power supply and a display.

The strip inserter 122 may be formed in a portion of the main body, and provided in a structure to which the test strip is to be inserted. However, a structure and design of the strip inserter 122 are not limited to the example described in the foregoing.

The plug 121 may be formed on one end surface of the main body, and provided in a structure that may be combined with or connected to the socket 111 of the blood glucose measuring device 110. As described above, the plug 121 may be provided as a phone jack plug or a pin plug, but not limited thereto.

The test strip may be formed with a material that absorbs blood.

For example, in a case in which the blood glucose measuring device 110 is embodied by a smartphone, the blood glucose measuring device 110 may execute a blood glucose measurement application. When the blood glucose measurement application is executed, the blood glucose measuring device 110 may determine whether the plug 121 of the blood glucose measuring module 120 is connected to the socket 111 of the blood glucose measuring device 110. When the connection of the blood glucose measuring module 120 to the blood glucose measuring device 110 is established, the blood glucose measuring module 120 may receive power from the power supply of the blood glucose measuring device 110, and run an internal test. When an abnormality is not detected from the internal test, the blood glucose measuring device 110 may display, through the display, a strip insertion screen that requests insertion of the test strip. When the test strip is inserted in the strip inserter 122 of the blood glucose measuring module 120 by a user, the blood glucose measuring device 110 may display a strip deterioration check screen that requests verification of whether the test strip is changed or not. When the test strip is determined to be normal, the blood glucose measuring device 110 may display, through the display, a blood injection screen that requests injection of blood.

When blood of the user is injected into the test strip, the blood glucose measuring module 120 may transmit, to the blood glucose measuring device 110, data indicating a blood glucose level in the blood. The blood glucose measuring device 110 may display a notification screen during the measuring of a blood glucose level, and calculate a result of the measuring of a blood glucose level in the blood based on the data transmitted from the blood glucose measuring module 120. The blood glucose measuring device 110 may display the calculated result of the measuring of a blood glucose level, and store the result.

Hereinafter, how the blood glucose measuring device 110 reads data received from the blood glucose measuring module 120 will be described in detail.

Figure 2:
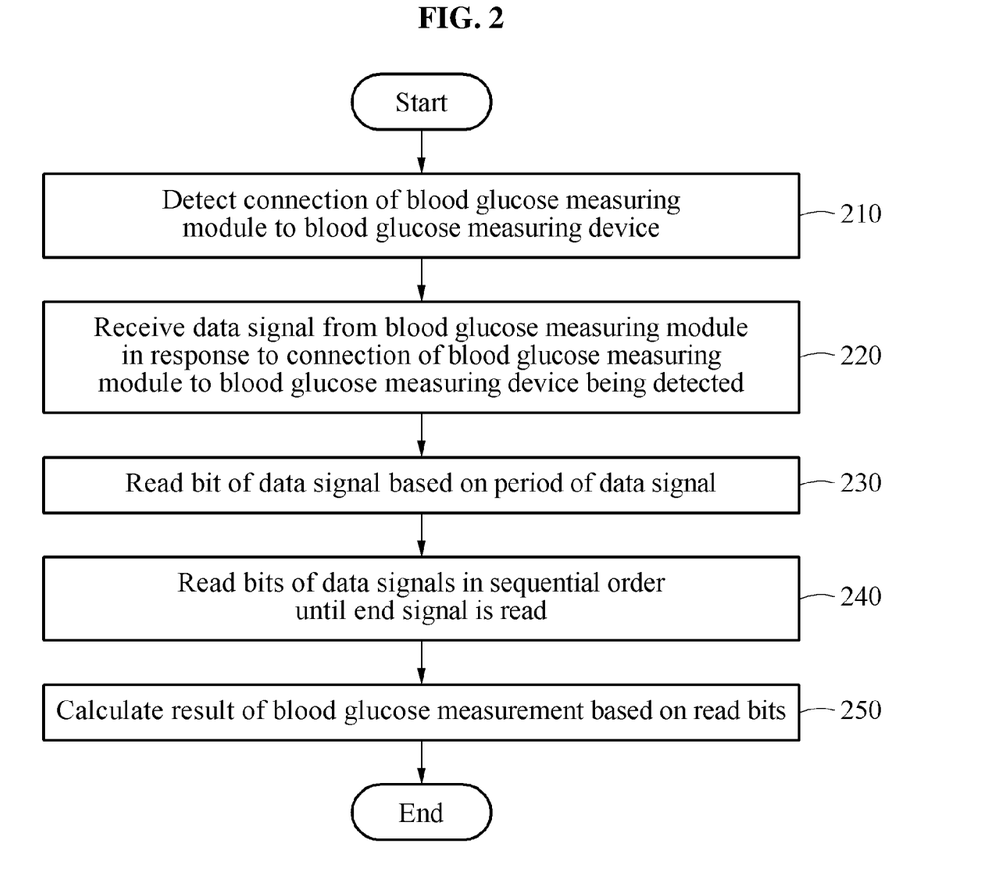
FIG. 2 is a flowchart illustrating an example of a blood glucose measuring method according to an example embodiment.

FIG. 2 is a flowchart illustrating an example of a blood glucose measuring method according to an example embodiment.

Referring to FIG. 2, in operation 210, a blood glucose measuring device detects a connection of a blood glucose measuring module to the blood glucose measuring device. For example, when a plug of the blood glucose measuring module and a socket of the blood glucose measuring device are connected, the blood glucose measuring device may establish communication with the blood glucose measuring module.

In operation 220, in response to the connection of the blood glucose measuring module to the blood glucose measuring device being detected, the blood glucose measuring device receives a data signal from the blood glucose measuring module. For example, the blood glucose measuring device may sample a magnitude of the data signal based on a preset sampling rate. The sampling rate may be, for example, 44100 hertz (Hz), but not limited thereto.

In operation 230, the blood glucose measuring device reads a bit indicated by the data signal based on a period of the data signal. For example, the blood glucose measuring device may estimate the period of the data signal from the data signal. The blood glucose measuring device may determine a bit mapped to the estimated period, and determine the bit indicated by the data signal. The data signal may indicate a bit value of 0 or 1.

In operation 240, the blood glucose measuring device reads bits of a series of data signals in sequential order until an end signal is read. For example, the blood glucose measuring device may receive sequence data including a start signal, a series of data signals, and an end signal. The blood glucose measuring device may read the bits of the data signals in sequential order until the end signal is received after the start signal is received.

In operation 250, the blood glucose measuring device calculates a result of measuring a blood glucose level based on the read bits. For example, the blood glucose measuring device may determine the result of measuring a blood glucose level based on a combination of the bits read from the data signals of the sequence data.

Figure 3:
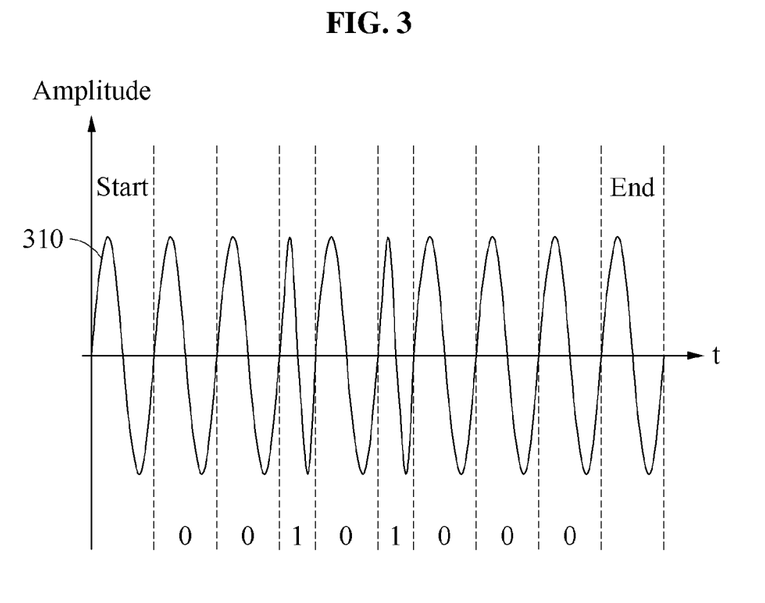
FIG. 3 is a graph illustrating an example of sequence data including a series of data signals according to an example embodiment.

FIG. 3 is a graph illustrating an example of sequence data including a series of data signals according to an example embodiment.

Referring to FIG. 3, sequence data 310 includes a start signal, a series of data signals, and an end signal. In the graph illustrated in FIG. 3, a horizontal axis indicates a time axis, and a vertical axis indicates a signal magnitude, for example, an amplitude, of a data signal. Herein, a single set of sequence data may include a preset number of data signals, and thus a blood glucose measuring device may be expected to receive a start signal, a preset number of data signals, and an end signal, in sequential order. In this example, eight data signals are illustrated as the series of data signals, and the sequence data 310 is 8 bits. However, the number of bits of the sequence data 310 is not limited to the example described in the foregoing, and the sequence data 310 may be embodied by n bits, excluding the start signal and the end signal, in which n denotes an integer greater than or equal to 1.

In addition, a preset bit may also be assigned to each of the start signal and the end signal. For example, 0 bit may be assigned to both the start signal and the end signal, but not limited thereto. Also, 1 bit may be assigned to both the start signal and the end signal, or different bits may be assigned to the start signal and the end signal, respectively, for example, (start signal, end signal)=(1, 0) and (start signal, end signal)=(0, 1).

Herein, when bits of the start signal and the end signal of the sequence data 310 differ from a preset combination of bits, the blood glucose measuring device may determine the sequence data 310 to be an error. For example, in a case in which at least one of the start signal or the end signal indicates 1 although bits of both the start signal and the end signal are set to be 0, the blood glucose measuring device may determine a corresponding data signal to ben an error signal.

The start signal, the data signals, and the end signal may include a periodic waveform. The periodic waveform may be, for example, a sinusoidal waveform, but not limited thereto. The sinusoidal waveform may indicate a sine waveform or a cosine waveform.

A bit of an individual signal may be classified based on a period of the signal. For example, a sinusoidal waveform of a first period may indicate a bit value of 0, and a sinusoidal waveform of a second period may indicate a bit value of 1.

For example, when a data signal has the first period, the blood glucose measuring device may determine a bit of the data signal to be 0. When the data signal has the second period different from the first period, the blood glucose measuring device may determine a bit of the data signal to be 1. For example, the second period may be set to be smaller than the first period, but not limited thereto.

The sequence data 310 illustrated in FIG. 3 will be described below as an example. An initially received signal having the first period may indicate a bit value of 0, and thus this signal may indicate a start signal. A series of data signals received afterwards may have the first period, the first period, the second period, the first period, the second period, the first period, the first period, and the first period, in sequential order as illustrated. Thus, this series of data signals may indicate data of "00101000." Herein, the series of data signals may indicate a blood glucose level. A lastly received signal having the first period may be received after the preset number of data signals is received, and thus indicate an end signal. The series of data signals may correspond to a bit sequence indicated by the sequence data 310, and indicate blood glucose level information.

Figure 4:
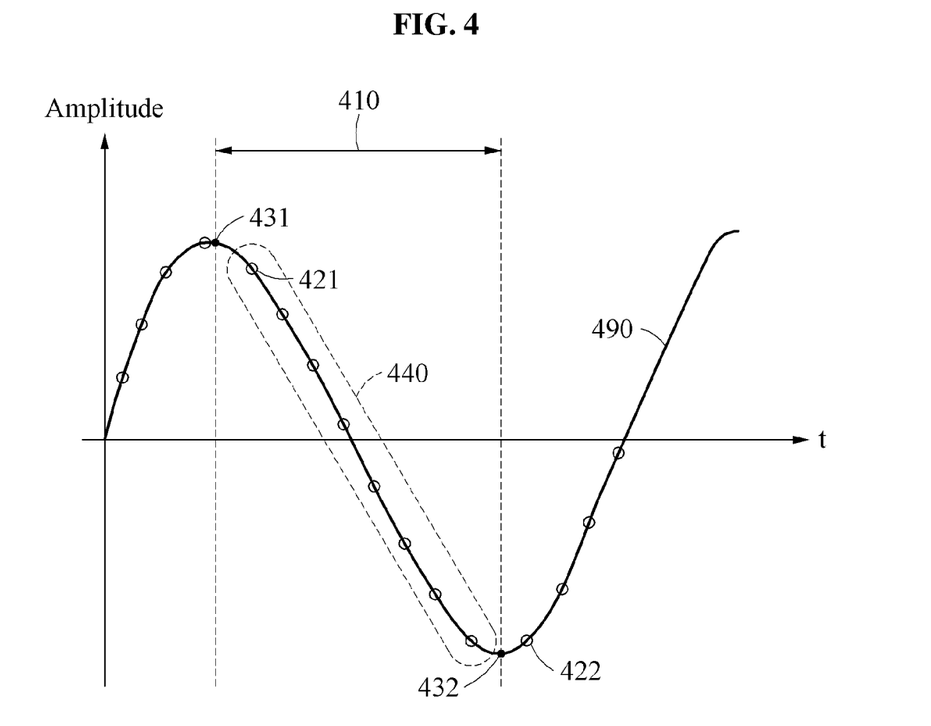
FIGS. 4 and 5 are graphs illustrating examples of a method of reading a bit of a data signal according to an example embodiment.
Figure 5:
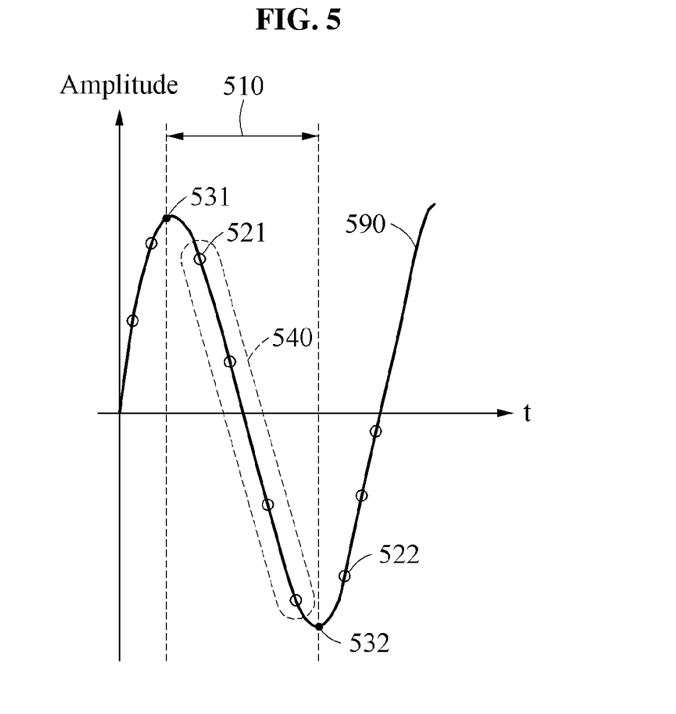

FIGS. 4 and 5 are graphs illustrating examples of a method of reading a bit of a data signal according to an example embodiment.

According to an example embodiment, a blood glucose measuring device may determine a period of a data signal based on a slope of a magnitude of the data signal. That is, the blood glucose measuring device may determine the period of the data signal based on a change in slope of the data signal.

For example, the blood glucose measuring device may determine a period of a data signal based on a change in slope sign of the data signal. The blood glucose measuring device may detect a first inflection point and a second inflection point based on a slope of the data signal, and determine the period of the data signal based on a time length between the first inflection point and the second inflection point. In this example, the blood glucose measuring device may determine a point at which a slope sign changes from (+) to (−) to be the first inflection point, and a point at which a slope sign changes from (−) to (+) to be the second inflection point.

The blood glucose measuring device may determine, to be a slope corresponding to a current timeslot of a data signal, a differential value indicating a difference between a signal magnitude corresponding to the current timeslot of the data signal and a signal magnitude corresponding to a previous timeslot of the data signal. Herein, a timeslot may be a time interval divided by a sampling rate, and the blood glucose measuring device may perform sampling on a data signal in each timeslot. A time point in the timeslot at which the sampling is performed may be referred to as a sampling point. For example, a middle point of the timeslot may be determined to be the sampling point.

For example, the blood glucose measuring device may determine the first inflection point and the second inflection point based on a point at which a differential value calculated with respect to the previous timeslot and a differential value calculated with respect to the current timeslot indicate different signs. In this example, when the differential value calculated with respect to the previous timeslot is a positive value and the differential value calculated with respect to the current timeslot is a negative value, the blood glucose measuring device may determine that the first inflection point is present in the current timeslot. When the differential value calculated with respect to the previous timeslot is a negative value and the differential value calculated with respect to the current timeslot is a positive value, the blood glucose measuring device may determine that the second inflection point is present in the current timeslot.

The first inflection point and the second inflection point may not accurately match sampling points. For example, for a data signal, a first inflection point may be present before a sampling point at which a sign is changed for the first time, and a second inflection point may be present before a sampling point at which a sign is changed for the second time.

The blood glucose measuring device may determine the period of the data signal based on the number of sampling points detected from an interval between the first inflection point and the second inflection point, which is referred to as a target interval. The blood glucose measuring device may determine the target interval based on the first inflection point at which a slope sign of the data signal is initially inverted and the second inflection point at which a slope sign of the data signal is secondly inverted. In detail, the blood glucose measuring device may count sampling points, starting from a sampling point at which the slope sign is initially changed up to a sampling point immediately before a sampling point at which the slope sign is secondly changed.

FIG. 4 illustrates a data signal 490 having a first period.

Referring to FIG. 4, the blood glucose measuring device determines a sampling point 421 at which a slope sign is initially changed, and a sampling point 422 at which the slope sign is secondly changed. The blood glucose measuring device determines a first inflection point 431 and a second inflection point 432 based on the sampling points 421 and 422 at which the slope sign is changed.

The blood glucose measuring device determines a target interval 410 based on a change in slope of the data signal 490, and determines a period of the data signal 490 based on the number of sampling points 440 detected in the target interval 410. The blood glucose measuring device determines the target interval 410 based on the first inflection point 431 and the second inflection point 432. However, the first inflection point 431 and the second inflection point 432 are not necessarily specified as points as used herein, and the blood glucose measuring device may also determine the target interval 410 based on the sampling points 421 and 422 at which the slope sign is changed.

When the number of sampling points 440 detected during the target interval 410 is in a first threshold range, the blood glucose measuring device may determine that the data signal 490 has a first period. The blood glucose measuring device may determine, to be 0, a bit value of the data signal 490 that is determined to have the first period.

For example, the first threshold range may indicate the number greater than or equal to th_num1, in which th_num1 denotes an integer greater than or equal to 1. In this example, th_num1 may be set to be 6. As illustrated in FIG. 4, eight sampling points are detected as the sampling points 440 in the target interval 410 and they are in the first threshold range, and thus the blood glucose measuring device may determine that the data signal 490 has the first period.

For another example, the first threshold range may indicate the number greater than or equal to m1 and less than or equal to m2, in which m1 and m2 denote an integer greater than or equal to 1. In this example, m1 and m2 may be set to be 7 and 8, respectively. As illustrated in FIG. 4, eight sampling points are detected as the sampling points 440 in the target interval 410 and they are in the first threshold range, and thus the blood glucose measuring device may determine that the data signal 490 has the first period. Thus, the blood glucose measuring device may determine a bit of the data signal 490 to be 0.

FIG. 5 illustrates a data signal 590 having a second period.

Referring to FIG. 5, the blood glucose measuring device determines a sampling point 521 at which a slope sign is initially changed, and a sampling point 522 at which a slope sign is secondly changed. The blood glucose measuring device determines a first inflection point 531 and a second inflection point 532 based on the sampling points 521 and 522 at which the slope sign is changed.

The blood glucose measuring device determines a target interval 510 based on the first inflection point 531 and the second inflection point 532. However, the first inflection point 531 and the second inflection point 532 are not necessarily specified as points as used herein, and the blood glucose measuring device may also determine the target interval 510 based on the sampling points 521 and 522 at which the slope sign is changed.

When the number of sampling points 540 detected during the target interval 510 is in a second threshold range, the blood glucose measuring device may determine that the data signal 590 has a second period. The blood glucose measuring device may determine, to be 1, a bit value of the data signal 590 that is determined to have the second period.

For example, the second threshold range may indicate the number less than or equal to th_num2, in which th_num2 denotes an integer greater than or equal to 1. In this example, th_num2 may be set to be 5. As illustrated in FIG. 5, four sampling points are detected as the sampling points 540 in the target interval 510 and they are in the second threshold range, and thus the blood glucose measuring device may determine that the data signal 590 has the second period.

For another example, the second threshold range may indicate the number greater than or equal to k1 and less than or equal to k2, in which k1 and k2 denote an integer greater than or equal to 1. In this example, k1 and k2 may be set to be 4 and 5, respectively. As illustrated in FIG. 5, four sampling points are detected as the sampling points 540 in the target interval 510 and they are in the second threshold range, and thus the blood glucose measuring device may determine that the data signal 590 has the second period. Thus, the blood glucose measuring device may determine a bit of the data signal 590 to be 1.

The first threshold range and the second threshold range may be determined in advance. For example, the blood glucose measuring device may determine the first threshold range and the second threshold range based on a device parameter. Thus, the blood glucose measuring device may set a threshold range optimized for a type of device, and provide a more accurate result of blood glucose measurement. In addition, the first threshold range and the second threshold range may be designed to include a margin.

However, how to set the first threshold range and the second threshold range is not limited to the examples described in the foregoing. Alternatively, the blood glucose measuring device may also determine the first threshold range and the second threshold range by receiving a pilot signal from the blood glucose measuring module during a calibration time in response to a connection of the blood glucose measuring module to the blood glucose measuring device, and determining the first threshold range and the second threshold range based on the number of sampling points detected during a target interval of the pilot signal. Herein, a preset pilot signal may be a signal predefined to allow the blood glucose measuring device and the blood glucose measuring module to communicate with each other during a calibration time. For example, the pilot signal may be a signal defined to indicate a bit sequence of "010" and "110." However, the bit sequence is provided merely as an example, and not limited to this example. Thus, the blood glucose measuring device may set the first threshold range and the second threshold range based on the number of the sampling points detected in the target interval of the pilot signal. For example, the blood glucose measuring device may determine the first threshold range to include an average of numbers of sampling points detected during target intervals of data signals of the pilot signal that have a first period. The blood glucose measuring device may also determine the second threshold range to include an average of numbers of sampling points detected during target intervals of data signals of the pilot signal that have a second period.

In the examples illustrated in FIGS. 4 and 5, the data signal 490 having the first period may have a frequency that is 16 times a sampling rate, and the data signal 590 having the second period may have a frequency that is 8 times the sampling rate. The first period may be twice the second period. However, the first period and the second period, and a frequency of each data signal, are not limited to the examples described in the foregoing, and may thus vary based on a design.

Figure 6:
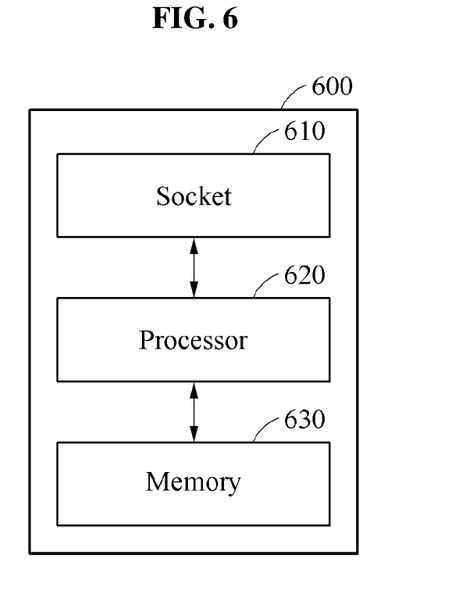
FIG. 6 is a diagram illustrating an example of a blood glucose measuring device according to an example embodiment.

FIG. 6 is a diagram illustrating an example of a blood glucose measuring device according to an example embodiment.

Referring to FIG. 6, a blood glucose measuring device 600 includes a socket 610, a processor 620, and a memory 630.

The socket 610 may include a structure that may be combined with or connected to a plug of a blood glucose measuring module configured to measure a blood glucose level. The socket 610 may be, for example, a microphone socket.

In response to a connection of the blood glucose measuring module to the socket 610 being detected, the processor 620 may receive a data signal from the blood glucose measuring module, and read a bit of the data signal based on a period of the data signal.

For example, after the connection of the blood glucose measuring module to the socket 610 is established and a start signal is received, the processor 620 may receive a series of data signals in sequential order until an end signal is received. In response to the data signal having a first period, the processor 620 may determine the bit of the data signal to be 0. In response to the data signal having a second period which is less than the first period, the processor 620 may determine the bit of the data signal to be 1.

In addition, in response to an inflection point not being detected from the data signal, the processor 620 may not perform an analysis of sequence data including the data signal. The data signal from which the inflection point is not detected may include noise, and thus the processor 620 may exclude the analysis of the data signal from which the inflection point is not detected and may thus prevent an error. For example, when an irregular data signal, for example, a signal without an inflection point, is detected due to noise and the like while data signals between the start signal and the end signal are being read, the processor 620 may determine the data signal to be an error. The blood glucose measuring device 600 may then skip reading of sequence data including the data signal that is determined to be an error, or perform rereading.

Further, the processor 620 may exclude, from reading, a sampling point that is not in a target interval of the data signal. For example, the processor 620 may determine the target interval based on sampling points detected within the target interval by excluding sampling points before a first inflection point and sampling points after a second inflection point from the data signal. Since interference and such by other neighboring data signals of each data signal may occur, as a communication delay, in a start interval and an end interval of each data signal, the blood glucose measuring device 600 may more accurately determine a period of a data signal based solely on such a target interval.

The operations of the processor 620 are not limited to the examples described in the foregoing, and thus the processor 620 may perform a combination of at least one of the operations described above with referenced to FIGS. 1 through 5.

The memory 630 may store, temporarily or semipermanently, information required to perform a blood glucose measuring method. For example, the memory 630 may store data signals, sequence data, blood glucose measurement results analyzed from the sequence data, and the like.

As described above, the blood glucose measuring device 600 may read a data signal based on a period of the data signal, and more accurately reduce an error in data reading that may occur due to noise, compared to when simply comparing, to a threshold value, a signal received by a microphone of a smartphone, for example.

According to example embodiments described herein, a blood glucose measuring module independent from a blood glucose measuring device may be compatible with various types of blood glucose measuring device, and thus a user may verify a blood glucose level of the user through the various types of blood glucose measuring device.

The blood glucose measuring device may read a bit based on a period of a data signal received from the blood glucose measuring module, and accurately analyze the data signal irrespective of an amplitude of the data signal.

The blood glucose measuring device may read the bit of the data signal based on the number of sampling points in a target interval of the data signal, and provide a result of data analysis robust against noise.

The blood glucose measuring device may exclude, from the analysis, a sampling point that is not in the target interval, and thus prevent an error in reading a bit that may occur due to a mixture with a previous signal.

The blood glucose measuring device may determine the target interval based on a slope of the data signal, and thus determine the target interval consistently despite noise.

A threshold range may be set differently based on a type of blood glucose measuring device, and thus accuracy in data analysis may be maintained for different types of blood glucose measuring device.

The blood glucose measuring device may analyze a signal having different two periods and clearly distinguish between data and noise, and thus ensure accuracy in data communication with the blood glucose measuring module.

The units described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A blood glucose measuring device comprising:
   a socket to be connected to a plug of a blood glucose measuring module configured to measure a blood glucose level; and
   a processor configured to:
   when a connection of the blood glucose measuring module to the socket is detected, receive a data signal from the blood glucose measuring module, determine a target interval based on a change in slope of the data signal, determine a period of the data signal based on an amount of sampling points detected in the target interval, and determine a value of zero or one for the data signal based on the period of the data signal.

2. The blood glucose measuring device of claim 1, wherein, after the connection of the blood glucose measuring module to the socket is established and a start signal is received, the processor is configured to receive a series of data signals in sequential order until an end signal is received.

3. The blood glucose measuring device of claim 1, wherein the processor is configured to:
   in response to the data signal having a first period, determine the value of zero or one of the data signal to be 0; and
   in response to the data signal having a second period different from the first period, determine the value of zero or one of the data signal to be 1.

4. The blood glucose measuring device of claim 1, wherein the processor is configured to determine the target interval based on a first inflection point at which a first slope sign of the data signal is initially inverted and a second inflection point at which a second slope sign of the data signal is secondly inverted.

5. The blood glucose measuring device of claim 1, wherein the processor is configured to:
   in response to the amount of sampling points detected during the target interval being in a first threshold range, determine the data signal to have a first period; and
   in response to the amount of sampling points detected during the target interval being in a second threshold range, determine the data signal to have a second period.

6. The blood glucose measuring device of claim 5, wherein the processor is configured to determine the first threshold range and the second threshold range based on a device parameter of the blood glucose measuring device.

7. The blood glucose measuring device of claim 5, wherein, in response to the connection of the blood glucose measuring module to the socket of the blood glucose measuring device being detected, the processor is configured to receive a pilot signal from the blood glucose measuring module during a calibration time, and determine the first threshold range and the second threshold range based on an amount of sampling points detected during a target interval of the pilot signal.

8. The blood glucose measuring device of claim 1, wherein, in response to an inflection point not being detected from the data signal, the processor is configured not to perform an analysis of sequence data including the data signal, the inflection point being any change or transition of data in the data signal.

9. The blood glucose measuring device of claim 1, wherein the processor is configured to exclude any sampling point that is not in the target interval of the data signal.

10. A blood glucose measuring method comprising:
    in response to a connection of a blood glucose measuring module to a socket of a computing device being detected, receiving, at the computing device, a data signal from the blood glucose measuring module; and
    with a processor of the computing device:
    determining a target interval based on a change in slope of the data signal;
    determining a period of the data signal based on an amount of sampling points detected in the target interval; and determining a value of zero or one for the data signal based on the period of the data signal.

11. A non-transitory computer-readable storage medium storing instructions that, when executed by a processor, cause the processor to perform the blood glucose measuring method of claim 10.

12. A blood glucose measuring system comprising:
a computing device; and
a blood glucose measuring module configured to measure a blood glucose level in blood absorbed in a test strip and, in response to being connected to the computing device, transmit a data signal indicating the measured blood glucose level to the computing device;
wherein the computing device is configured to, in response to the connection to the blood glucose measuring module, receive the data signal, determine a target interval based on a change in slope of the data signal, determine a period of the data signal based on an amount of sampling points detected in the target interval, and determine a value of zero or one for the data signal based on the period of the data signal.

* * * * *